United States Patent
Crawford et al.

(10) Patent No.: US 9,668,772 B1
(45) Date of Patent: Jun. 6, 2017

(54) ATLANTOAXIAL JOINT REPLACEMENT DEVICE

(71) Applicants: Neil Robert Crawford, Tempe, AZ (US); Anna G. U. S. Newcomb, Chandler, AZ (US); Phillip M. Reyes, Mesa, AZ (US); Seungwon Baek, Phoenix, AZ (US); Nicholas Theodore, Paradise Valley, AZ (US)

(72) Inventors: Neil Robert Crawford, Tempe, AZ (US); Anna G. U. S. Newcomb, Chandler, AZ (US); Phillip M. Reyes, Mesa, AZ (US); Seungwon Baek, Phoenix, AZ (US); Nicholas Theodore, Paradise Valley, AZ (US)

( * ) Notice: Subject to any disclaimer, the term of this patent is extended or adjusted under 35 U.S.C. 154(b) by 140 days.

(21) Appl. No.: 14/065,375

(22) Filed: Oct. 28, 2013

(51) Int. Cl.
*A61B 17/70* (2006.01)

(52) U.S. Cl.
CPC ................. *A61B 17/7011* (2013.01)

(58) Field of Classification Search
CPC ............ A61B 17/7032; A61B 17/7034; A61B 17/701; A61B 17/7011
USPC .......................................... 606/246–261, 278
See application file for complete search history.

(56) References Cited

U.S. PATENT DOCUMENTS

| 5,531,745 A * | 7/1996 | Ray ................. A61B 17/7055 606/261 |
| 7,931,676 B2 * | 4/2011 | Veldman ........... A61B 17/7005 606/246 |
| 2011/0172711 A1 * | 7/2011 | Kirschman ........ A61B 17/7058 606/252 |

* cited by examiner

*Primary Examiner* — Ellen C Hammond
*Assistant Examiner* — Christina Negrellirodrigue
(74) *Attorney, Agent, or Firm* — Booth Udall Fuller, PLC

(57) ABSTRACT

Disclosed is an atlantoaxial joint replacement device and method that allows up to full normal axial rotation while stabilizing C1-C2 vertebrae. The device includes a rail member curved in a circular path with a path of curvature oriented in an axial plane. The rail member includes a track body having a non-circular cross-sectional shape. A rider member is slidingly coupled to the rail member and includes a body defining a through slot that receives there through the rail member. The through slot has a non-circular cross-sectional shape compatible to the non-circular cross-sectional shape of the track body of the rail member.

20 Claims, 3 Drawing Sheets

ATLANTOAXIAL JOINT REPLACEMENT DEVICE

BACKGROUND

Technical Field

This document relates to an atlantoaxial joint replacement device and method for restoring stability while allowing axial rotation.

Background

The atlantoaxial joint includes the first and second cervical vertebrae (C1-C2 vertebrae) and their intervening ligaments. This joint of the spine is unique in that it has no intervertebral disc, with the primary articulating surfaces being the left and right facet articulations. The atlantoaxial joint allows an extremely large amount of axial rotational motion (~90° bilateral). This quantity of motion is by far the most of any single level in the spine, and accounts for more than half of the axial rotation of the entire neck. Such large motion is allowed by the pivoting of C1 about the vertically oriented odontoid process (dens) of C2. This motion is similar to rotation of a wheel on its axis, hence C1 is also referred to as the "atlas" and C2 is also referred to as the "axis".

Throughout the entire range of motion during left and right axial rotation at C1-C2, the axis serves as a fixed center of rotation. This joint is therefore more hinge-like than other joints of the spine where the center of rotation is not necessarily fixed, but instead may shift to different positions at different phases of motion. C1 is kept centered on the axis by being sandwiched between the anterior bony arch of C1 anteriorly, and the horizontal cruciate ligament (transverse atlantal ligament) posteriorly.

Injury or other pathological occurrence can make C1-C2 unstable. In such instances, risk of neurological injury is high. Some injuries that destabilize the C1-C2 joint are surgically treatable, such as fracture of the dens. In this particular case, a screw may be used to repair the fracture, reattaching the dens peg to the body of C2 so that the hinge-like joint is again functional.

However, most other injuries to C1-C2 are treated instead by fusion. Typically, for fusion, the surgeon attaches screws and rods posteriorly to immobilize C1-C2 and places or wires a bone graft in apposition to the surfaces of C1 and C2 so that eventually the level becomes fused. However, such surgery has the consequence that more than half of the patient's neck rotation is restricted.

SUMMARY

Aspects of this document relate to an atlantoaxial joint replacement surgical implant device that is capable of restoring stability at C1-C2 after it has become destabilized through injury, degeneration, or surgical intervention. This atlantoaxial joint replacement device is motion sparing and, therefore, does not limit a patient's ability to rotate their neck postoperatively.

These aspects may comprise, and implementations may include, one or more or all of the components and steps set forth in the appended CLAIMS.

In one aspect, an atlantoaxial joint replacement device is disclosed. The atlantoaxial joint replacement device may include a rail member curved in a circular path with a path of curvature oriented in an axial plane, the rail member including a track body having a non-circular cross-sectional shape. A rider member may be slidingly coupled to the rail member, the rider member including a body defining a through slot that receives there through the rail member, the through slot having a non-circular cross-sectional shape compatible to the non-circular cross-sectional shape of the track body of the rail member.

Particular implementations may include one or more or all of the following.

The body of the rider member may further include a first leg extending out from a side of the body and a second leg extending out from an opposite side of the body.

A distal free end of each leg may include a rod portion.

The rail member and the rider member may be formed from different biocompatible materials. The biocompatible materials may be a metal and a polymer or a ceramic and a polymer.

Distal free ends of the rail member may each include a rod portion.

The through slot of the rider member may include a longitudinally elongated through slot that allows a predetermined amount of longitudinal translation of the rail member therein. The predetermined amount of longitudinal translation of the rail member within the longitudinally elongated through slot may be about 1-5 mm.

The rail member may be sized and positioned to achieve a center of rotation at a dens location of the C2 vertebra during axial rotation.

In another aspect, an atlantoaxial joint replacement device is disclosed that allows up to full normal axial rotation while stabilizing C1-C2 vertebrae. The atlantoaxial joint replacement device may include a rail member coupled to one of the C1-C2 vertebrae, the rail member curved in a circular path with a path of curvature oriented in an axial plane, the rail member including a track body having a non-circular cross-sectional shape. A rider member may be coupled to a different one of the C1-C2 vertebrae and slidingly coupled to the rail member, the rider member including a body defining a through slot that receives there through the rail member, the through slot having a non-circular cross-sectional shape compatible to the non-circular cross-sectional shape of the track body of the rail member.

Particular implementations may include one or more or all of the following.

The rail member and the rider member may be formed from different biocompatible materials.

The through slot of the rider member may include a longitudinally elongated through slot that allows a predetermined amount of longitudinal translation of the rail member therein.

The rail member or the rider member may be coupled to lateral masses of the C1 vertebra using at least one screw in each lateral mass.

The rail member or the rider member may be coupled to pars or pedicles of the C2 vertebra using at least one screw in each par or pedicle.

The rail member may be sized and positioned to achieve a center of rotation at a dens location of the C2 vertebra during axial rotation.

In still another aspect, a method of stabilizing C1-C2 vertebrae is disclosed that allows up to full normal axial rotation by surgically implanting from a posterior approach an atlantoaxial joint replacement device. The method may include: coupling a rail member to one of the C1-C2 vertebrae, the rail member curved in a circular path with a path of curvature oriented in an axial plane, the rail member comprising a track body having a non-circular cross-sectional shape; and coupling a rider member slidingly coupled to the rail member to a different one of the C1-C2 vertebrae, the rider member comprising a body defining a through slot that receives there through the rail member, the through slot having a non-circular cross-sectional shape compatible to the non-circular cross-sectional shape of the track body of the rail member.

Particular implementations may include one or more or all of the following.

Coupling a rail member to one of the C1-C2 vertebrae may include coupling the rail member or the rider member to lateral masses of the C1 vertebra using at least one screw in each lateral mass.

Coupling a rider member to a different one of the C1-C2 vertebrae may include coupling the rail member or the rider member to pars or pedicles of the C2 vertebra using at least one screw in each par or pedicle.

The foregoing and other aspects, features, and advantages will be apparent to those of ordinary skill in the art from the DESCRIPTION and DRAWINGS, and from the CLAIMS.

BRIEF DESCRIPTION OF DRAWINGS

Implementations will hereinafter be described in conjunction with the appended DRAWINGS (which are not necessarily to scale), where like designations denote like elements, and.

DESCRIPTION

Figure 1:
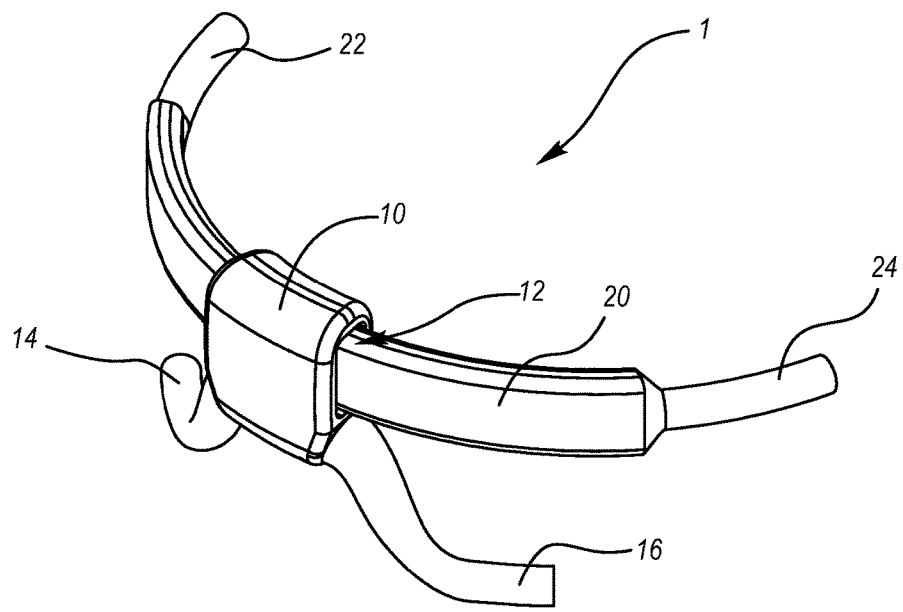
FIG. 1 is a posterolateral perspective view of an implementation of an atlantoaxial joint replacement device.
Figure 2:
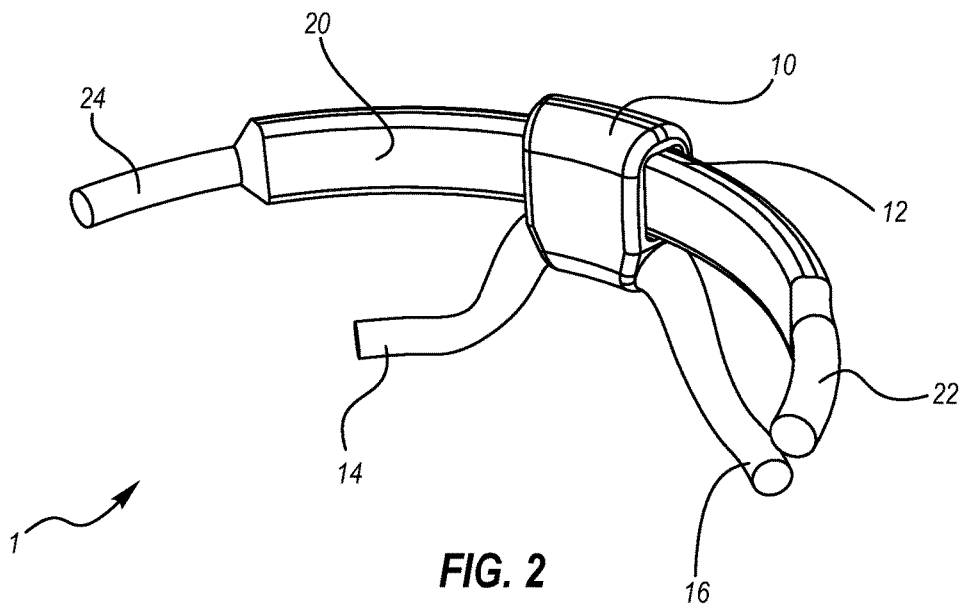
FIG. 2 is an anterolateral perspective view of the atlantoaxial joint replacement device of FIG. 1.

This document features an atlantoaxial joint replacement device that is surgically implanted from a posterior approach and that restores stability at the atlantoaxial joint of the spine (C1-C2 vertebrae), while still allowing as much as the normal range of axial rotational motion.

There are many features of atlantoaxial joint replacement device and method implementations disclosed herein, of which one, a plurality, or all features or steps may be used in any particular implementation.

In the following description, reference is made to the accompanying DRAWINGS which form a part hereof, and which show by way of illustration possible implementations. It is to be understood that other implementations may be utilized, and structural, as well as procedural, changes may be made without departing from the scope of this document. As a matter of convenience, various components will be described using exemplary materials, sizes, shapes, dimensions, and the like. However, this document is not limited to the stated examples and other configurations are possible and within the teachings of the present disclosure.

Structure

There are a variety of atlantoaxial joint replacement device implementations that allow up to full normal axial rotation while stabilizing C1-C2. An atlantoaxial joint replacement device may generally include a curved rail member that is coupled to either one of the C1 and C2 vertebrae and a rider member that is coupled to the other C1 and C2 vertebrae and that slides along the rail member. For example, the rail member may be coupled to C1 lateral masses using at least one screw in each lateral mass and the rider member may be coupled to C2 pars or pedicles using at least one screw in each side.

The curvature of the rail may be such that the center of rotation during axial rotation remains located at the normal position of the dens (odontoid process). Thus, the rail may be curved in a circular path, with the path of curvature oriented in the transverse or axial plane.

Accordingly, the atlantoaxial joint replacement device allows ample axial rotation, but generally disallows rotation in other planes or translation in any plane, although considerations for small amounts of motion in other directions are given. To this end for example, the cross-section of the rail member may be a non-circular geometry and a through-hole of the rider member may mate closely with the rail member.

Notwithstanding, turning to FIGS. 1-4 and for the exemplary purposes of this disclosure, atlantoaxial joint replacement device 1 is shown. Atlantoaxial joint replacement device 1 may include two separate members: rider member 10 and curved rail member 20.

Rider member 10 includes a body with a through slot 12 and legs 14 and 16 extending from the body. The distal free ends of each leg 14 and 16 includes a rod portion for mounting to the head of a screw (with locking caps or nuts for example) inserted in the C1 or C2 vertebrae depending upon how atlantoaxial joint replacement device 1 is mounted to C1-C2. Through slot 12 is configured to receive there through and slideably engage with rail member 20 and may have any rectilinear or curvilinear cross-section, for example circular, oval, square, rectangular, or other geometry. A non-circular cross-section would prevent binding of rider member 10 on rail member 20 in case of forces that might try to rotate C1 about C2 in flexion-extension or lateral bending planes (i.e., planes besides axial rotation). For example, a rectangular cross-section would block such rotations. With rectilinear cross-sections, the through slot 12 may include rounded or beveled edges.

Curved rail member 20 includes a track body with opposing distal free ends 22 and 24 each including a rod portion for mounting to the head of a screw (with locking caps or nuts for example) inserted in the C1 or C2 vertebrae depending upon how atlantoaxial joint replacement device 1 is mounted to C1-C2. The track body of curved rail member 20 may have any rectilinear or curvilinear cross-section substantially corresponding to the shape of slot 12, for example circular, oval, square, rectangular, or other geometry. A non-circular cross-section would prevent binding of rider member 10 on rail member 20 in case of forces that might try to rotate C1 about C2 in flexion-extension or lateral bending planes (i.e., planes besides axial rotation). For example, a rectangular cross-section would block such rotations. With rectilinear cross-sections, the track body of rail member 20 may include rounded or beveled edges.

Figure 3:
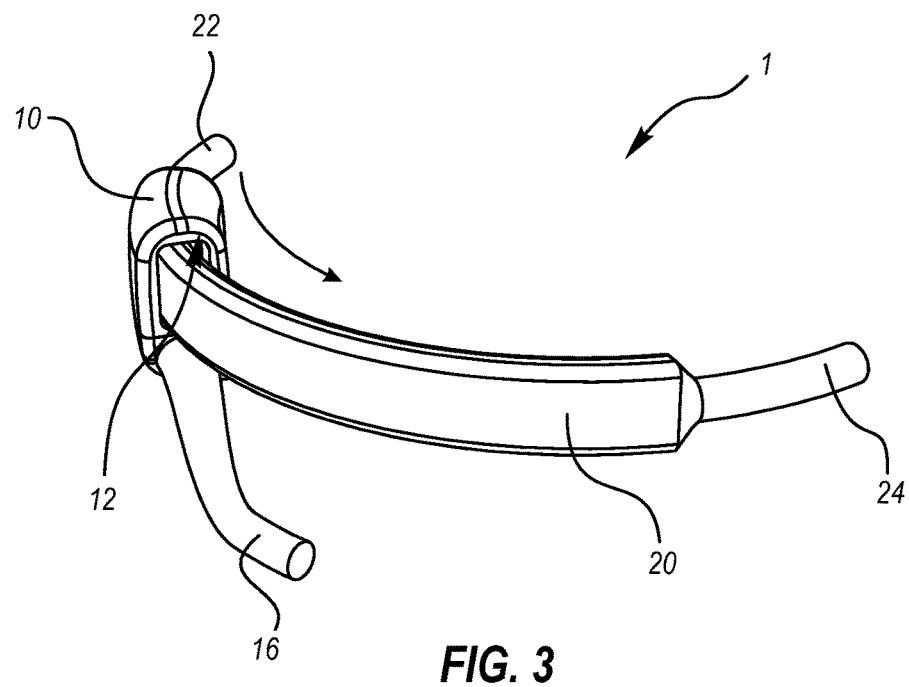
FIGS. 3 and 4 are lateral and posterior perspective views of the atlantoaxial joint replacement device of FIG. 1 depicting sliding rotation of a rider member along a rail member.
Figure 4:
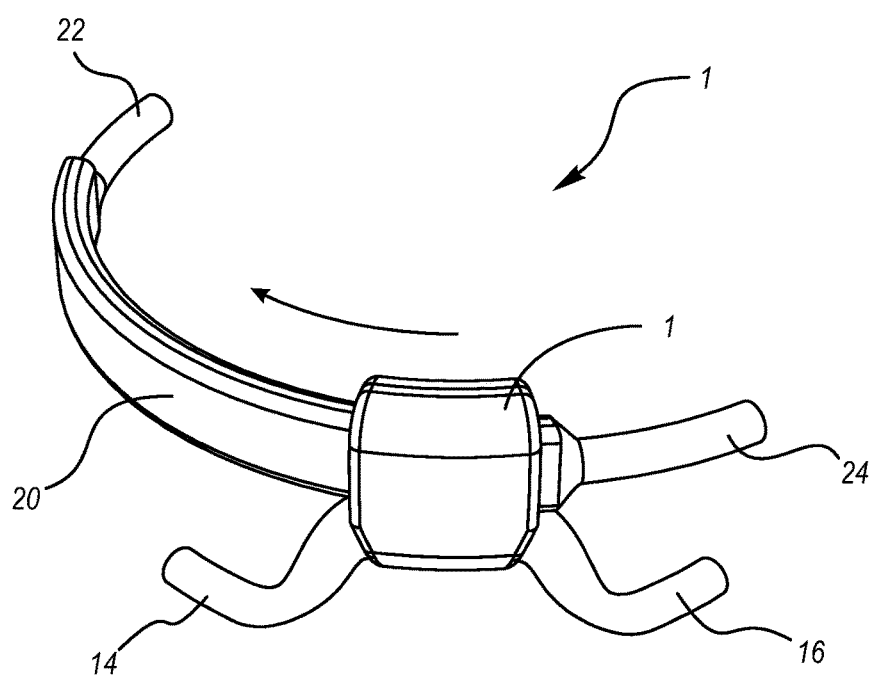

Turning to FIGS. 3-4 and with atlantoaxial joint replacement device 1 coupled to the atlantoaxial joint of the spine (C1-C2 vertebrae), as the neck rotates axially to the left, rider member 10 slides along curved rail member 20 until rider member 10 reaches a stop near the left end of curved rail member 20. As the neck rotates axially to the right, rider member 10 slides on curved rail member 20 until it reaches a stop near the right end of curved rail member 20. It is not possible for C1 to translate on C2 or to rotate about any other axis because rail member 20 and rider member 10 prevent these other motions. The stops encountered at the end of rotation may be screws holding rail member 20 in place or they may be stops designed into the ends of rail member 20. These stops, if screw heads or other protrusions, may provide a stiff, abrupt stop. It is possible to introduce a more flexible stop through selection of the material used for rider member 10 and/or through usage of non-metallic stops, such as elastic "bumpers".

Additional Embodiments

There are many additional implementations atlantoaxial joint replacement devices.

For the exemplary purposes of this disclosure, among the many ways for mounting rider or rail members of implementations of an atlantoaxial joint replacement device to C1, screw attachments with lateral mass screws may be employed for example since the lateral masses are very prominent on C1. On C2, it is possible to mount the other rider or rail member of the atlantoaxial joint replacement device in many ways as well. One option is through C2 pars screws. Other possibilities in addition to or in place of pars screws are C2 pedicle screws, C2 lateral mass screws, C2 intralaminar screws, and/or C2 spinous process screws. If mounted using screws, it is possible for screws to go through holes in the atlantoaxial joint replacement device; then, when the screws are tightened, the atlantoaxial joint replacement device is then drawn up tight against the bone. Or, screws could be inserted first and then the atlantoaxial joint replacement device locked into the screw heads with locking caps or nuts. For example, the screws could be standard top-loading tulip head screws, such as used with the Harms/Goel Technique for fusion. A commercially available example of such top-loading tulip head screws is the Vertex Select Reconstruction System by Medtronic Spinal and Biologics, Memphis, Tenn.

For the exemplary purposes of this disclosure, other possible ways of mounting implementations of an atlantoaxial joint replacement device are by wiring, clamping, or gluing for example. For example, some implementations of an atlantoaxial joint replacement device may be attached to bone using adhesive or by chemically accelerated ingrowth of bone into pores in the metallic surfaces instead of using screws.

For the exemplary purposes of this disclosure, one possible long-term complication of the implanted atlantoaxial joint replacement device could be loosening at the attachment-bone interfaces. To prevent such an occurrence, certain steps could be taken. One possibility is to increase the number of points of fixation. For example, an additional screw could be inserted into the spinous process of C2 instead of using screws only in the C2 pars, pedicles, or lateral masses. Or, multiple screws could be inserted into each C1 lateral mass, since the lateral masses are large. Or, fixation to the C2 lamina using intralaminar screws could be used in addition to pars/pedicle screws. Or, pars/pedicle and lateral mass screws could be used together in C2. Another possibility is to use bony ingrowth into the hardware surface (porous coating), or increased formation of bony overgrowth by application of a bone growth promoter such as BMP or electrical or magnetic stimulation to enhance bone growth. Another possibility is to enhance the fixation of the screws using augmentation such as cement around the screw, cement injected through fenestrations in the screw, or hardware features otherwise anchoring the screw, such as drywall type anchors.

For the exemplary purposes of this disclosure, in some implementations of an atlantoaxial joint replacement device a laterally (horizontally) oriented hinge may be included in the rail, rider, screw-rail interface, or screw-rider interface to allow some flexion and extension.

For the exemplary purposes of this disclosure, another possible long-term complication of the implanted atlantoaxial joint replacement device is tissue ingrowth into the sliding region (the area where the rider member slides over the rail member). For example, in some implementations of an atlantoaxial joint replacement device may include a protective sheath to prevent tissue ingrowth into the sliding region. For example, in some implementations of an atlantoaxial joint replacement device the rider and rail members may be coated with a material that prevents overgrowth. In yet other implementations of an atlantoaxial joint replacement device, for example, intermittent electrical stimulation may be applied to the device of an amplitude and frequency that might prevent tissue formation or ablate any newly formed tissue that might have been deposited. In still other implementations of an atlantoaxial joint replacement device, for example, a membrane may be incorporated to cover the sliding region. Such a membrane could be accordion-like, encompassing the entire assembly, so that portions of the accordion membrane compress or expand as the rider member moves, or the membrane could be fixed, but with a slot on one side to cover the majority but not all of the sliding region or device.

For the exemplary purposes of this disclosure, it is important that the surgeon be able to appropriately position atlantoaxial joint replacement devices to achieve the desired center of rotation. An offset center of rotation could lead to unwanted impingement on the spinal cord during rotation. In some implementations of an atlantoaxial joint replacement device mechanisms for adjustment may be incorporated into the rail member, rider member, or both. Adjustments could be made using set screws for example at the screw-rail interface, screw-rider interface, or rider-rail interface enabling the surgeon to adjust/reposition the anteroposterior, rostrocaudal, and lateral position of the rail and rider members in situ (during surgical placement).

For the exemplary purposes of this disclosure, preoperative or intraoperative planning could be used to identify the correct positioning and size of atlantoaxial joint replacement devices. For example, a computed tomography image could be used to identify the anatomy and current location of the odontoid process. The correct radius of curvature of an atlantoaxial joint replacement device could then be selected based on the distance from the posterior elements to the odontoid in these medical images. Screw locations and lengths could be pre-planned so that the atlantoaxial joint replacement device would be inserted in the correct position. Screws could then be inserted using image guidance through optical tracking, as is currently done for other techniques in the same region such as C1-C2 transarticular screws or odontoid fracture repair screws.

For the exemplary purposes of this disclosure, the rider member must slide across the rail member through numerous daily cycles. Such behavior would be expected to generate wear debris, which may have a negative effect on surrounding tissues and should be minimized. Different material interfaces could be used to minimize wear debris. In some implementations of an atlantoaxial joint replacement device, for example, a ceramic flange may be incorporated on the rider member or cover on the rail member to provide a metal-on-ceramic interface, which should have good wear debris properties. Or, the flange on the rider/cover on rail could be formed of polyethylene or other polymer to enable a metal-on-polymer interface.

For the exemplary purposes of this disclosure, in some implementations of an atlantoaxial joint replacement device the rail and rider members are free to move in the axial rotation direction of angular motion, but in other directions motion is limited by the rail-rider interface. It is possible to introduce an aspect of flexibility into this interface and, therefore, in resistance to motions other than axial rotation through the materials selected for the components or through flanges or other components. For example, a flange in the rider slot may be made of polyethylene and would experience some "give" or flexibility when loaded against a hard metal rail member for example. This flexibility would be greater than if the interface were metal-on-metal.

For the exemplary purposes of this disclosure, although the primary consideration is for an atlantoaxial joint replacement device to allow only axial rotation, it may also be desirable for the device to allow angular motion in other planes and translation in certain directions. For example, in the literature, longitudinal (vertical) translation has been described as occurring together with axial rotation at C1-C2. The literature also reports some normal flexion/extension at C1-C2. These other motions could be introduced into implementations of an atlantoaxial joint replacement device as well.

For example, for vertical translation, instead of being tight-fit, the rider member's slot may be a longitudinally (vertically) elongated through slot that allows longitudinal (vertical) translation of the rail member, thus allowing the rider member to slide up and down in the slot (allowing some longitudinal/vertical translation). Alternatively, a longitudinally/vertically oriented linear sliding mechanism may be included in the rail, rider, screw-rail interface, or screw-rider interface to allow vertical translation. For example, there could be a shaft in a mated tube where the rider member meets its base that has a linear bearing. Either such mechanism could introduce a desired amount of longitudinal/vertical translation (about 1-5 mm).

For example, for flexion and extension, the rider member could have a ring that may or may not be spring-loaded that allows the rider member to rotate about the rail member instead of only sliding along the rail member. Alternatively, the interface where the rail member attaches to bone could have a pivot, allowing the rail member to move relative to the bone, thereby allowing flexion/extension and also some lateral bending. Because of the distance from the rail member to the anterior region of C1/C2, such mechanisms would secondarily allow some vertical translation at the odontoid during flexion/extension.

For the exemplary purposes of this disclosure, in some implementations an atlantoaxial joint replacement device it may be desirable to interconnect an atlantoaxial joint replacement device implementation to a motion-sparing prosthesis or fusion device at adjacent levels (C0-C1 or C2-C3). Possible secondary devices could be a posterior C0-C1 transarticular screw fixation construct, posterior C0-C1 plate, posterior C2-C3 (or C2-farther caudal level) screw-rod construct, or posterior C2-C3 facet prosthesis. For example, interlocking mechanisms such as threaded sockets, mating parts, through-holes, or slotted channels in the rider member and/or rail member may be used to interconnect the atlantoaxial joint replacement device to such fusion or arthroplasty at adjacent rostral and/or caudal levels.

Other implementations are within the CLAIMS.

Specifications, Materials, Manufacture, Assembly

It will be understood that implementations are not limited to the specific components disclosed herein, as virtually any components consistent with the intended operation of an atlantoaxial joint replacement device implementation may be utilized. Accordingly, for example, although particular components and so forth, are disclosed, such components may comprise any shape, size, style, type, model, version, class, grade, measurement, concentration, material, weight, quantity, and/or the like consistent with the intended operation of an atlantoaxial joint replacement device implementation. Implementations are not limited to uses of any specific components, provided that the components selected are consistent with the intended operation of an atlantoaxial joint replacement device implementation.

Accordingly, the components defining any atlantoaxial joint replacement device implementation may be formed of any of many different types of materials or combinations thereof that can readily be formed into shaped objects provided that the components selected are consistent with the intended operation of an atlantoaxial joint replacement device implementation. For example, the components may be formed of: rubbers (synthetic and/or natural) and/or other like materials; ceramics and/or other like materials; polymers such as thermoplastics (such as ABS, Fluoropolymers, Polyacetal, Polyamide; Polycarbonate, Polyethylene, Polyether ether ketone (PEEK), Polysulfone, and/or the like), thermosets (such as Epoxy, Phenolic Resin, Polyimide, Polyurethane, Silicone, and/or the like), any combination thereof, and/or other like materials; composites and/or other like materials; metals, such as zinc, magnesium, titanium, copper, iron, steel, carbon steel, alloy steel, tool steel, stainless steel, spring steel, aluminum, any combination thereof, and/or other like materials; alloys, such as aluminum alloy, titanium alloy, magnesium alloy, copper alloy, cobalt-chromium alloy, any combination thereof, and/or other like materials; any other suitable material; and/or any combination thereof.

For the exemplary purposes of this disclosure, rail and rider member implementations may be made of any material such as polymers, metals, composites, ceramics, and/or the like. The material(s) may be picked so as to make the rail and rider members have any desirable attribute such as strength, lightweight, durability, and so forth. In one implementation, the rail and rider members may be constructed from biocompatible materials such as metal-on-polymer (e.g. polyethylene). In other implementations of an atlantoaxial joint replacement device other low-wear biomaterials such as ceramic, polycarbonate, or PEEK may form the rail or rider or form an articulating layer—flange or coating—at the rail/rider interface.

Various atlantoaxial joint replacement device implementations may be manufactured using conventional procedures as added to and improved upon through the procedures described here. Some components defining atlantoaxial joint replacement device implementations may be manufactured simultaneously and integrally joined with one another, while other components may be purchased pre-manufactured or manufactured separately and then assembled with the integral components.

Manufacture of these components separately or simultaneously may involve extrusion, pultrusion, vacuum forming, injection molding, blow molding, resin transfer molding, casting, forging, cold rolling, milling, drilling, reaming, turning, grinding, stamping, cutting, bending, welding, soldering, hardening, riveting, punching, plating, and/or the like. If any of the components are manufactured separately, they may then be coupled with one another in any manner, such as with adhesive, a weld, a fastener (e.g. a bolt, a nut, a screw, a nail, a rivet, a pin, and/or the like), wiring, any combination thereof, and/or the like for example, depending on, among other considerations, the particular material forming the components.

It will be understood that the assembly of atlantoaxial joint replacement device implementations are not limited to the specific order of steps as disclosed in this document. Any steps or sequence of steps of the assembly of atlantoaxial joint replacement device implementations indicated herein are given as examples of possible steps or sequence of steps and not as limitations, since various assembly processes and sequences of steps may be used to assemble atlantoaxial joint replacement device implementations.

Use

Implementations of an atlantoaxial joint replacement device are particularly useful for atlantoaxial joint replacements that are surgically implanted from a posterior approach and that restore stability at the atlantoaxial joint of the spine (C1-C2 vertebrae), while still allowing as much as the normal range of axial rotational motion, as previously explained. However, implementations are not limited to these particular uses. Rather, any description relating to joint replacement applications is for the exemplary purposes of this disclosure, and implementations may also be used in a variety of other applications with similar results.

Figure 5:
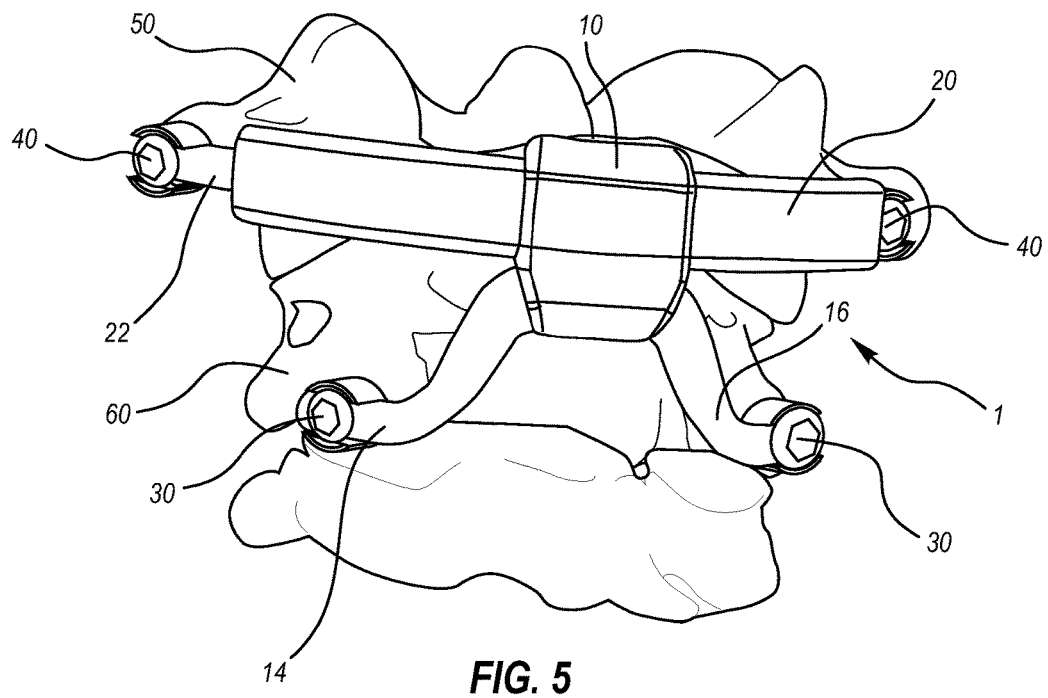
FIG. 5 is an in use posterior perspective view of the atlantoaxial joint replacement device of FIG. 1 coupled to the atlantoaxial joint of the spine (C1-C2 vertebrae)
Figure 6:
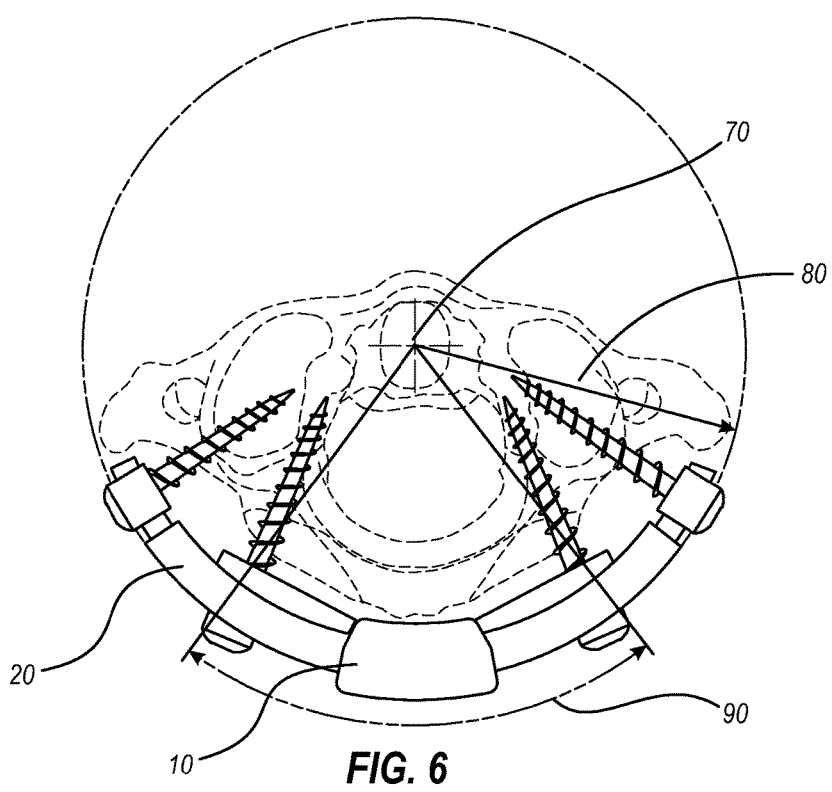
FIG. 6 is an in use superior view of the atlantoaxial joint replacement device of FIG. 1 coupled to the atlantoaxial joint of the spine (C1-C2 vertebrae) depicting a circular path of curvature oriented in the transverse or axial plane with the center of rotation during axial rotation remaining located at the normal position of the dens (odontoid process).

In describing the use of atlantoaxial joint replacement device implementations further and for the exemplary purposes of this disclosure, reference is made to FIGS. 5-6 and atlantoaxial joint replacement device 1.

Turning to FIG. 5, atlantoaxial joint replacement device 1 may be surgically implanted from a posterior approach. It is important that the surgeon be able to appropriately position atlantoaxial joint replacement device 1 to achieve the desired center of rotation. An offset center of rotation could lead to unwanted impingement on the spinal cord during rotation. Preoperative or intraoperative planning could be used to identify the correct positioning and size of atlantoaxial joint replacement device 1. For example, a computed tomography image could be used to identify the anatomy and current location of the odontoid process. The correct radius of curvature of atlantoaxial joint replacement device 1 could then be selected based on the distance from the posterior elements to the odontoid in these medical images. Screw locations and lengths could be pre-planned so that atlantoaxial joint replacement device 1 would be inserted in the correct position. Screws could then be inserted using image guidance through optical tracking, as is currently done for other techniques in the same region such as C1-C2 transarticular screws or odontoid fracture repair screws.

Specifically, atlantoaxial joint replacement device 1 may be coupled to the atlantoaxial joint of the spine (C1-C2 vertebrae). It is possible either for the curved rail 20 to be attached to C1 and the rider member 10 to C2, or for the curved rail member 20 to be attached to C2 and the rider member 10 to C1. The implementation described and illustrated here will be for the curved rail member 20 to be attached to C1 50 with lateral mass screws 40 since the lateral masses are very prominent on C1 50. The screws 40 are inserted first and then the rod portions of distal free ends 22 and 24 are mounted to the heads of screws 40 with locking caps or nuts. On C2 60, rider member 10 may be mounted through pars screws 30 for example. As with C1, the screws 30 are inserted first and then the distal free rod portions of each leg 14 and 16 are mounted to the heads of screws 30 with locking caps or nuts.

Referring now to FIG. 6, the radius of curved rail member 20 and the position of curved rail member 20 relative to the anatomy of C1 and rider member 10 will dictate the center of rotation 70 of the joint during axial rotation. It is known from the spinal literature that the center of rotation 70 during axial rotation is normally at the dens (odontoid process) and so appropriate positioning and sizing of hardware will maintain this position 70 even if the odontoid or surrounding structures are absent. Thus, a circular path of curvature is oriented in the transverse or axial plane having a center of rotation 70 during axial rotation remaining located at the normal position of the dens (odontoid process) and having a radius of curvature 80 that accommodates/fits C1 therein.

Once atlantoaxial joint replacement device 1 is coupled to the atlantoaxial joint of the spine (C1-C2 vertebrae), such a configuration allows extreme rotation sometimes reaching 90° (±45°). As the neck rotates axially to the left, rider member 10 slides along curved rail member 20 until rider member 10 reaches a stop near the left end of curved rail member 20. As the neck rotates axially to the right, rider member 10 slides on curved rail member 20 until it reaches a stop near the right end of curved rail member 20. It is not possible for C1 to translate on C2 or to rotate about any other axis in this implementation because rail member 20 and slot 12 of rider member 10 have compatible rectangular cross-sectional shapes that prevent these other motions. The stops encountered at the end of rotation may be the heads of screws 40 holding rail member 20 in place.

In places where the description above refers to particular implementations, it should be readily apparent that a number of modifications may be made without departing from the spirit thereof and that these implementations may be alternatively applied. The accompanying CLAIMS are intended to cover such modifications as would fall within the true spirit and scope of the disclosure set forth in this document. The presently disclosed implementations are, therefore, to be considered in all respects as illustrative and not restrictive, the scope of the disclosure being indicated by the appended CLAIMS rather than the foregoing DESCRIPTION. All changes that come within the meaning of and range of equivalency of the CLAIMS are intended to be embraced therein.

The invention claimed is:

1. An atlantoaxial joint replacement device comprising:
   a rail member curved in a circular path with a path of curvature oriented in an axial plane around a vertical axis extending through both C1-C2 vertebrae at a dens location (odontoid process), the rail member comprising:
      a track body having a non-circular cross-sectional shape,
      a first distal free end coupled to a first lateral mass screw, and
      a second distal free end coupled to a second lateral mass screw; and
   a rider member slidingly coupled to the rail member, the rider member comprising a body defining a through slot through which the rail member is disposed, the through slot having a vertically elongated non-circular cross-sectional shape compatible to the non-circular cross-sectional shape of the track body of the rail member that introduces 1-5 mm of vertical translation of the rider member relative to the rail member, the rider member further comprising:
      a first leg extending out from a first side of the rider member and coupled to a first par screw, and a second leg extending out from a second side of the rider member opposite the first side and coupled to a second par screw; and wherein the atlantoaxial joint replacement device provides up to 90° (±45°) of bilateral axial rotational motion while stabilizing the C1-C2 vertebrae.

2. The device of claim 1 wherein each of the first distal free end and the second distal free end comprises a rod portion.

3. The device of claim 1, wherein the rail member and the rider member are formed from different biocompatible materials.

4. The device of claim 3, wherein the biocompatible materials are a metal and a polymer or a ceramic and a polymer.

5. The device of claim 1, wherein the first distal free end and the second distal free end of the rail member each comprise a rod portion.

6. The device of claim 1, wherein the rail member is sized and positioned to achieve a center of rotation at the dens location of the C2 vertebra during axial rotation.

7. An atlantoaxial joint replacement device, comprising:
a rail member coupled to one of C1-C2 vertebrae, the rail member curved in a circular path with a path of curvature oriented in an axial plane around a vertical axis through the C1-C2 vertebrae, the rail member comprising a track body having a non-circular cross-sectional shape; and
a rider member coupled to a different one of the C1-C2 vertebrae and slidingly coupled to the rail member when in use, the rider member comprising a body defining a through slot that receives there through the rail member, the through slot having a non-circular cross-sectional shape compatible to the non-circular cross-sectional shape of the track body of the rail member, the rider member further comprising:
a first leg extending out from a first side of the rider member, and
a second leg extending out from a second side of the rider member opposite the first side; and
wherein the atlantoaxial joint replacement system provides up to full bilateral axial rotational motion while stabilizing C1-C2 vertebrae.

8. The device of claim 7, wherein the rail member and the rider member are formed from different biocompatible materials.

9. The device of claim 7, wherein the through slot of the rider member comprises a longitudinally elongated through slot that allows a predetermined amount of longitudinal translation of 1-5 mm of the rail member therein.

10. The device of claim 7, wherein the rail member or the rider member is coupled to lateral masses of the C1 vertebra using at least one screw in each lateral mass.

11. The device of claim 7, wherein the rail member or the rider member is coupled to pars or pedicles of the C2 vertebra using at least one screw in each par or pedicle.

12. The device of claim 7, wherein the rail member is sized and positioned to achieve a center of rotation at a dens location of the C2 vertebra during axial rotation.

13. The device of claim 7, wherein the atlantoaxial joint replacement system provides up to about 90° (±45°) of bilateral axial rotational motion while stabilizing C1-C2 vertebrae.

14. The device of claim 7, the rail member further comprising:
a first distal free end coupled to a first screw; and
a second distal free end coupled to a screw.

15. A method of stabilizing two vertebrae comprising:
coupling a rail member to one of the two vertebrae, the rail member curved in a circular path with a path of curvature oriented in an axial plane around an axis of the two vertebrae, the rail member comprising a track body having a non-circular cross-sectional shape; and
coupling a rider member slidingly coupled to the rail member to a different one of the two vertebrae, the rider member comprising a body defining a through slot that receives there through the rail member, the through slot having a non-circular cross-sectional shape compatible to the non-circular cross-sectional shape of the track body of the rail member;
wherein stabilizing the two vertebrae allows axial rotation by surgically implanting from a posterior approach the rail member and the rider member.

16. The method of claim 15, wherein coupling a rail member to one of the two vertebrae comprises coupling the rail member or the rider member to lateral masses of the one vertebra using at least one screw in each lateral mass.

17. The method of claim 15, wherein coupling a rider member to a different one of the two vertebrae comprises coupling the rail member or the rider member to pars or pedicles of the different one of the vertebra using at least one screw in each par or pedicle.

18. The method of claim 15, wherein the rail member and the rider member provide up to full bilateral axial rotational motion while stabilizing the two vertebrae.

19. The method of claim 15, wherein the axis of the two vertebrae is a vertical axis extending through the two vertebrae.

20. The method of claim 15, further comprising:
a first leg extending out from a first side of the rider member, and
a second leg extending out from a second side of the rider member opposite the first side.

* * * * *